(12) United States Patent
Picaud et al.

(10) Patent No.: US 9,308,260 B2
(45) Date of Patent: Apr. 12, 2016

(54) ANTICONVULSIVE PHARMACEUTICAL COMPOSITIONS

(75) Inventors: Serge Picaud, Avon (FR); Jose Alain Sahel, Paris (FR); Jammoul Firas, Bagneux (FR); Caroline Coriat, Paris (FR); Manuel Simonutti, Paris (FR)

(73) Assignee: INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 899 days.

(21) Appl. No.: 12/667,742

(22) PCT Filed: Jul. 4, 2008

(86) PCT No.: PCT/EP2008/058672
§ 371 (c)(1),
(2), (4) Date: Jan. 5, 2010

(87) PCT Pub. No.: WO2009/004082
PCT Pub. Date: Jan. 8, 2009

(65) Prior Publication Data
US 2010/0184707 A1 Jul. 22, 2010

(30) Foreign Application Priority Data

Jul. 5, 2007 (EP) .................................. 07301208
Feb. 22, 2008 (EP) .................................. 08151851

(51) Int. Cl.
*A61K 45/06* (2006.01)
*A61K 31/185* (2006.01)
*A61K 31/197* (2006.01)

(52) U.S. Cl.
CPC ............... *A61K 45/06* (2013.01); *A61K 31/185* (2013.01); *A61K 31/197* (2013.01)

(58) Field of Classification Search
CPC A61K 31/185; A61K 31/197; A61K 2300/00
USPC .......... 514/18, 562, 46, 222.5, 315, 114, 311, 514/252, 326, 455, 479, 217, 249
See application file for complete search history.

(56) References Cited

U.S. PATENT DOCUMENTS

| 6,713,497 B1 | 3/2004 | Ashby, Jr. |
| 2005/0129783 A1 | 6/2005 | McCleary et al. |

FOREIGN PATENT DOCUMENTS

EP          1 407 785          4/2004

OTHER PUBLICATIONS

Louzada.. FASEB Journal, 2004, 18, 511-18.*
Jantzen and Robinson. Modern Pharmaceutics, 1996, p. 596.*
"Metabolite-encyclopedia.com", http://www.encyclopedia.com/topic/metabolite.aspx#1-1E1 :metabolit-full, accessed Jan. 25, 2008.*
Gladkevich, A., "The peripheral GABAergic system as a target in endocrine disorders." Autonomic Neuroscience 124.1 (2006): 1-8.*
Hogema, B. M., "Pharmacologic rescue of lethal seizures in mice deficient in succinate semialdehyde dehydrogenase." Nature genetics 29.2 (2001): 212-216.*
Della Pietra, G.,"In vivo conversion of gamma-hydroxybutyrate into gamma-aminobutyrate." Nature 210.5037 (1966): 733-734.*
OHSU Investigates Similarities Between Rare Genetic Disorder and Rave Party Drug, Sep. 9, 2001, OSHU Communications; accessed online Jul. 28, 2014; http://www.ohsu.edu/xd/about/news_events/news/2001/09-02-ohsu-researchers-investi.cfm.*
Seiler, N., "Synergistic anticonvulsant effects of GABA-T inhibitors and glycine." Naunyn-Schmiedeberg's archives of pharmacology 326.1 (1984): 49-57.*
Vigabatrin, From Wikipedia, the free encyclopedia; accessed online Aug. 4, 2014; http://en.wikipedia.org/wiki/Vigabatrin.*
Emri, Z., "Gamma-hydroxybutyric acid decreases thalamic sensory excitatory postsynaptic potentials by an action on presynaptic GABA<sub>B</sub> receptors." Neuroscience letters 216.2 (1996): 121-124.*
Panayiotopoulos, C. P., "Elementary visual hallucinations, blindness, and headache in idiopathic occipital epilepsy: differentiation from migraine." Journal of Neurology, Neurosurgery & Psychiatry 66.4 (1999): 536-540.*
Froger, N., "Taurine: The comeback of a neutraceutical in the prevention of retinal degenerations." Progress in retinal and eye research 41 (2014): 44-63.*
Berson, E. L., "Retinal degeneration in cats fed casein. II. Supplementation with methionine, cysteine, or taurine." Investigative Ophthalmology & Visual Science 15.1 (1976): 52-58.*
V.Yu. Smirnov et al., "Metabolic Effects of Mixture Containing Branched-Chain Amino Acids and Taurine during Subchronic Poisoning with Barbiturates" Bulletin of Experimental Biology and Medicine, vol. 137, No. 5, May 2004, XP002462441, ISSN: 0007-4888, pp. 443-446.
Jorge Muhling et al., "Effects of Propofol and Taurine of Intracellular Free Amino Acid Profiles nd Immune Function Markers in Neutrophils in Vitro", Clinical Chemistry and Laboratory Medicine, Walter De Gruyter UND CO, DE, XPVol. 40, No. 2, 2002, XP008086698, ISSN: 1434-6621 pp. 111-121.
Huang, Fenghe et al., "Anticonvulsant effect of taurine and its influence on GABA and taurine level in brain mice", XP002462443, retrieved from STN, Database accession No. 1996:207287 abstract & Guangdong Yaoxueyuan Xuebao, 11(4), 220-3 CODEN GyXUF8, 1995.

(Continued)

*Primary Examiner* — Samantha Shterengarts
*Assistant Examiner* — Matt Mauro
(74) *Attorney, Agent, or Firm* — Young & Thompson (57) ABSTRACT

The use of substance selected from taurine, a taurine precursor, a taurine metabolite, a taurine derivative, a taurine analog and a substance required for the taurine biosynthesis, for preventing or inhibiting the undesirable side-effects caused to a human or an animal organism by an active ingredient that induces a high level of extracellular GABA or increases GABA receptor activation, and a pharmaceutical composition including the substance and the active ingredient.

3 Claims, 4 Drawing Sheets

(56) References Cited

OTHER PUBLICATIONS

Schmidt S. Y. et al., "Retinal degeneration in cats fed casein. III. Taurine deficiency and ERG amplitudes", Investigative Ophthalmology and Visual Science 1997 United States, vol. 16, No. 7, 1977, XP002462442, ISSN: 0146-0404, pp. 673-678.

E. Anyanwu et al., "The involvement of taurine in the action mechanism of sodium valproate (VPA) in the treatment of epilepsy" Acta Physiologica, Pharmacologica Et Therapeutica Latinoamericana, Asociacion Latinoamericana De Ciencias Fisiologicas Buenous Ai, Ar, vol. 43, No. 1-2, 1993, XP008086580, ISSN: 0327-6309, pp. 20-27.

International Search Report dated Dec. 19, 2008, from corresponding PCT application.

* cited by examiner

ANTICONVULSIVE PHARMACEUTICAL COMPOSITIONS

FIELD OF THE INVENTION

The present invention relates to the field of human or animal therapy using anticonvulsive active ingredients that induce a high level of extracellular GABA or activate GABA receptors. These active anticonvulsive ingredients are used for preventing various neurological disorders including epilepsy.

More particularly, this invention is aimed at reducing the undesirable effects caused to a human or an animal organism by these anticonvulsive active ingredients, including damages to the retina.

BACKGROUND OF THE INVENTION

GABA is important to several neurological disorders, including Parkinson's disease, Huntington's chorea, Alzheimer's disease, and epilepsy, a central nervous system disease characterized by recurring convulsive seizures.

A deficiency of GABA in the brain has been implicated as one cause for convulsions. (Karlsson, A.; Funnum, F.; Malthe-Sorrensen, D.; Storm-Mathisen, J. Biochem Pharmacol 1974, 22, 3053-3061.) In an effort to raise the concentration of GABA in the brain, both direct injection and oral administration of GABA have been studied. It was shown that injection of GABA into the brain has an anticonvulsant effect, but it is obviously not a practical method. Taking GABA orally, however, is not effective because GABA cannot cross the blood-brain barrier, a membrane protecting the CNS from xenobiotics in the blood.

To correct the deficiency of brain GABA and therefore stop convulsions, an important approach is to use an inhibitor of GABA-aminotransferase (GABA-AT) that is able to cross blood-brain barrier. (Nanavati, S. M.; Silverman, R. B. J. Med. Chem. 1989, 32, 2413-2421.). Inhibition of this enzyme increases the concentration of GABA in the brain, which has therapeutic applications in epilepsy as well as other neurological disorders. One of the most effective in vivo time-dependent inhibitors of GABA-AT is 4-amino-5-hexenoic acid, which is also termed gamma-vinyl GABA or vigabatrin, an anticonvulsant drug marketed almost all over the world.

Other ways for correcting the deficiency of brain GABA relies on increasing GABA transmission by blocking GABA transporters like tiagabine, acting at GABA receptors (topiramate or felbamate) or activating the glutamate decarboxylase to increase GABA synthesis (pyridoxal phosphate, valproate, gabapentin). All strategies have in common to increase the concentration of GABA in the brain or directly activate its receptors and thus stimulate GABA therapeutic effects in various neurological disorders including epilepsy.

Regarding more particularly epilepsy, even though existing antiepileptic drugs can render 80% of newly diagnosed patients seizure free, a significant number of patients have chronic intractable epilepsy causing disability with considerable socioeconomic implications.

Anti-epileptic drugs are available for treating epilepsies, but these agents have a number of shortcomings. For instance, the agents are often poorly soluble in aqueous and biological fluids or are extremely hygroscopic. Of even greater importance is that patients often become refractory to a drug over time. In addition, many anti-epileptic agents cause unwanted side effects, neurotoxicities, and drug interactions. Even while being treated with one or a combination of the anti-epileptic drugs currently in clinical use, 30% of epileptic patients still experience seizures. As more anti-epileptic drugs are developed, the clinician will have expanded pharmaceutical options when designing an effective treatment protocol for each patient.

Vigabatrin, which was developed as an inhibitor of gamma-aminobutyric acid transaminase, was one of the most promising novel anticonvulsant active ingredients. However, vigabatrin, like some other compounds that increase GABA levels, can induce highly severe undesirable effects, such as an irreversible constriction of the visual field. The constriction of the visual field induced by vigabatrin is asymptomatic when it is restricted to the nasal quadrant, until it extends to more central areas. Furthermore, visual defects induced by vigabatrin are not limited to the constriction of the visual field but also includes dysfunction of central vision with a reduction of visual acuity, a loss of color discrimination and of contrast sensitivity. An arrest of a therapeutical treatment with vigabatrin allows a stabilization of the visual loss but very rarely induces any recovery.

However, because epileptic seizures are always very handicapping and may be lethal, active ingredients that increase the GABA levels, including vigabatrin, are still prescribed. Similarly, visual side effects were also described with many other anti-epileptic molecules blocking the GABA transaminase (valproate), increasing GABA levels by blocking GABA transporter (tiagabine), stimulating GABA synthesis and/or release (gabapentin, valproate, levetiracetam), or increasing GABA receptor activation (topiramate, felbamate, benzodiazepines like diazepam, clonazepam and clobazam or barbiturates like primidone and phenobarbitone).

There is thus a need in the art for substances or methods that would allow avoiding side effects that are caused to the human or animal organisms which are treated by anticonvulsive active ingredients that increase GABA levels or activate GABA receptors.

There is thus a need in the art for improved anticonvulsive, including anti-epileptic, pharmaceutical treatments based on anticonvulsive active ingredients, which would be endowed with reduced or no undesirable effects.

SUMMARY OF THE INVENTION

The present invention provides for the use of taurine, a taurine precursor, a taurine metabolite, a taurine derivative, a taurine analog and a substance required for the taurine biosynthesis, for manufacturing a pharmaceutical composition for preventing or inhibiting the undesirable side-effects caused to a human or an animal organism by an active ingredient that induces an increase of extracellular GABA or GABA transmission.

Preferred active ingredients that induce a high level of extracellular GABA, for which side effects are prevented or inhibited, are selected from the group consisting of GABA-aminotransferase inhibitors, GABA transport inhibitors, GABA receptor activators and glutamate decarboxylase activators.

The most preferred active ingredient, for which side effects are prevented or inhibited, consists of 4-amino-5-hexenoic acid, also termed vigabatrin. The active ingredient is either the racemic mixture or the active isomer.

This invention also provides for pharmaceutical compositions comprising, as the active ingredients, a combination of:
(i) a first active ingredient that induces a high level of extracellular GABA or increases GABA transmission; and
(ii) a second active ingredient selected from the group consisting of taurine, a taurine precursor, a taurine metabolite, a taurine derivative, a taurine analog and a substance required for the taurine biosynthesis, and one or more pharmaceutically acceptable excipients.

The present invention also pertains to a method for treating convulsive disorders, including epilepsy, comprising a step of administering, to a patient in need thereof, a combination of:

(i) a first active ingredient that induces a high level of extracellular GABA or increases GABA transmission; and (ii) a second active ingredient selected from the group consisting of taurine, a taurine precursor, a taurine metabolite, a taurine derivative, a taurine analog and a substance important for taurine biosynthesis like vitamin B6.

BRIEF DESCRIPTION OF THE FIGURES

When rats (FIG. 1A) and mice (FIG. 1B) were treated with vigabatrin, a supplementation with taurine or vitamin B6 prevented or partially suppressed the decrease in amplitude of the photopic electroretinogram (ERG) observed under vigabatrin alone. The differences in the photopic ERG amplitudes were statistically significant between the control and vigabatrin treated animals (VGB: * $p<0.05$). By contrast, in mice, the differences between control animals and animals treated with vigabatrin plus taurine or vigabatrin plus vitamin B6 were no longer significant. In rats, the difference remained significant with the control group (VGB+ taurine: * $p<0.05$). However, in both mice and rats, animals receiving vigabatrin plus taurine had smaller decrease in photopic ERG amplitude than animals treated with vigabatrin alone; the differences were statistically significant (VGB+ taurine, ° $p<0.05$). Similarly, mice receiving vitamin B6 supplementation in addition to vigabatrin had smaller decrease in photopic ERG than with vigabatrin alone and the difference was statistically significant (VGB+ B6, ° $p<0.05$).

A) Taurine plasma levels in control and vigabatrin-treated animals in each group. B) Correlation between taurine plasma levels and the photopic ERG amplitude in VGB-treated control rats. The correlation factor between these two factors is equal to 0.769 ($p=0.0093\%$, $n=10$). C) Correlation between the taurine plasma levels and the density of inner/outer cone photoreceptor segments. The correlation factor between these two parameters is equal to 0.818 ($p=0.0038\%$, $n=10$). D) Correlation between the photopic ERG amplitudes and the density of inner/outer cone photoreceptor segments. The correlation factor between these two factors is equal to 0.703 ($p=0.0023\%$, $n=10$). E) Recovery of taurine plasma levels by taurine supplementation in VGB-treated rats. In A and E, the horizontal line represents the mean value.

Quantification of photopic ERG amplitude (3A), length of retinal areas with displaced photoreceptor nuclei (3B), density of cone inner/outer segments (3C) and areas with increased GFAP expression (3D) in control rats (s.e.m., n=6), in the VGB-treated animals with or without taurine supplementation (VGB, n=7; VGB+taurine, n=7, s.e.m.). The scale bar represents 50 μm (IPL: inner plexiform layer).

Quantification of photopic ERG amplitude (4A), length of retinal areas with displaced photoreceptor nuclei (4B), density of cone inner/outer segments (4C) and areas with bipolar cell sprouting into the ONL (4D) in control mice (s.e.m., n=5), in VGB-treated animals with or without taurine supplementation (VGB, s.e.m., n=7; VGB+taurine, s.e.m., n=7). The scale bar represents 50 μm (IPL: inner plexiform layer).

DETAILED DESCRIPTION OF THE INVENTION

Surprisingly, it has been found according to the invention that the progressive and irreversible loss of visual acuity of patients treated with the extracellular GABA inducer vigabatrin is associated with a high decrease in circulating taurine concentration. Notably, a taurine deficiency has been found in Vigabatrin-treated epileptic infants.

It has also been shown according to the invention that there is a correlation between low taurine plasma levels found in the Vigabatrin-treated rats and the loss of visual functions in the said animals.

It has also been surprisingly found herein that a supplementation of vigabatrin-treated individuals with taurine or with a substance required for the taurine biosynthesis inhibits the vigabatrin-induced undesirable side effects, and inhibits particularly the vigabatrin-induced retinal lesions.

These inventor's findings were all the more surprising that it was previously shown in the art that vigabatrin induced no change in the levels of taurine, whereas it induced a three-fold increase in GABA levels.

It has thus been found according to the invention that the deleterious side effects that are caused by anticonvulsive active ingredients acting as extracellular GABA-inducers might be prevented or blocked by the administration of any one of the substances that increase the amount of circulating taurine within a human or an animal organism.

As intended herein, the substances that increase the amount of circulating taurine within a human or an animal organism encompass, in addition to taurine per se, also taurine precursors, taurine metabolites, taurine derivatives, taurine analogs and substances required for the taurine biosynthesis.

As intended herein, taurine precursors, taurine metabolites, taurine derivatives, taurine analogs and substances required for the taurine biosynthesis may be collectively termed "taurine-like" substances.

Thus, an object of the present invention consists of the use of a substance selected from the group consisting of taurine, a taurine precursor, a taurine metabolite, a taurine derivative, a taurine analog and a substance required for the taurine biosynthesis, for manufacturing a pharmaceutical composition for preventing or inhibiting the undesirable side-effects caused to a human or an animal organism by an active ingredient that induces a high level of extracellular GABA.

As used herein, taurine consists of the 2-aminoethanesulfonic acid.

As used herein, taurine precursors encompass substances that, when they are administered to a human or an animal, can be transformed, directly or indirectly, into taurine.

Preferred taurine precursors are selected from the group consisting of cysteine, cystathionine, homocysteine, S-adenosylhomocysteine, serine, N-acetyl-cysteine, glutathione, N-formylmethionine, S-adenosylmethionine, betaine and methionine.

As used herein, taurine metabolites encompass substances that are produced in vivo by transformation of taurine.

Preferred taurine metabolites are selected from the group consisting of hypotaurine, thiotaurine, taurocholate.

As used herein, taurine derivatives encompass substances that are structurally close to taurine but possess at least one structural difference, such as one or more chemical changes, e.g. at least one replacement of an atom or a chemical group found in taurine by a distinct atom or a distinct chemical group.

Preferred taurine derivatives are selected from different entities including the group consisting of acetylhomotaurinate, and piperidino-, benzamido-, phthalimido- or phenylsuccinylimido taurine derivatives. Such taurine derivatives are described notably by Kontro et al. (1983, Prog Clin Biol Res, Vol. 125: 211-220) and by Andersen et al. (2006, Journal of pharmaceutical Sciences, Vol. 73(n °1): 106-108). Derivatives include for instance taurolidine (4,4'-methylene-bis(tetrahydro-2H-1,2,4-thiadiazine-1,1-dioxide or taurolin), taurultam and taurinamide, chlorohydrate-N-isopropylamide-2-(1-phenylethyl)aminoethanesulfonic acid.

As used herein, taurine analogs encompass substances that are chemically distinct from taurine but which exert the same biological activity, e.g. an inhibition of the retinal lesions induced by the extracellular GABA inducer vigabatrin.

Preferred taurine analogs are selected from the group consisting of (+/−)piperidine-3-sulfonic acid (PSA), 2-aminoethylphosphonic acid (AEP), (+/−)2-acetylaminocyclohexane sulfonic acid (ATAHS), 2-aminobenzenesulfonate (ANSA), hypotaurine, ±trans-2-aminocyclopentanesulfonic acid (TAPS) 8-tétrahydroquinoléine sulfonic acid (THQS), N-2-hydroxyethylpiperazine-N'-2-ethane sulphonic acid (HEPES), beta-alanine, glycine, guanidinoethylsulfate (GES), 3-acétamido-1-propanesulfonic acid (acamprosate).

As used herein, the substances required for taurine biosynthesis encompass all substances that are involved in the in vivo taurine biosynthesis including enzymes and enzyme cofactors, thus including cysteine dioxygenase (EC 1.13.11), sulfinoalanine decarboxylase (EC 4.1.1.29) and cofactors thereof.

Preferred substances required for taurine biosynthesis are selected from the group consisting of vitamin B6 (or pyridoxal-5'-phosphate), vitamin B12 (cobalamin), folic acid, riboflavin, pyridoxine, niacin, thiamine (thiamine pyrophosphate) and pantothenic acid.

As used herein, active ingredients that induce a high level of extracellular GABA or increases GABA receptor activation encompass GABA-aminotransferase inhibitors, GABA transporter inhibitors, Glutamate decarboxylase activators and GABA receptor agonists or modulators.

GABA-aminotransferase, may also be termed GABA-transaminase or 4-aminobutyrate transaminase (EC 2.6.1.19). Glutamate decarboxylase is classified as EC 4.1.1.15.

As intended herein, GABA-aminotransferase inhibitors, the side effects of which are inhibited or blocked by taurine, encompass is 4-amino-5-hexenoic acid (vigabatrin), valproate, (1R,3S,4S)-3-amino-4-fluorocyclopentane-1-carboxylic acid, (1R,4S)-4-amino-2-cyclopentene-1-carboxylic acid, (1S,4R)-4-amino-2-cyclopentene-1-carboxylic acid, (4R)-4-amino-1-cyclopentene-1-carboxylic acid, (4S)-4-amino-1-cyclopentene-1-carboxylic acid, (S)-4-amino-4,5-dihydro-2-thiophenecarboxylic acid, 1H-tetrazole-5-(alpha-vinyl-propanamine), 2,4-Diaminobutanoate, 2-Oxoadipic acid, 2-Oxoglutarate, 2-Thiouracil, 3-Chloro-4-aminobutanoate, 3-Mercaptopropionic acid, 3-Methyl-2-benzothiazolone hydrazone hydrochloride, 3-Phenyl-4-aminobutanoate, 4-ethynyl-4-aminobutanoate, 5-Diazouracil, 5-Fluorouracil, Aminooxyacetate, beta-Alanine, Cycloserine and D-Cycloserine.

As intended herein; glutamate decarboxylase activators, the side effects of which can be inhibited or blocked by taurine, encompass 2-Oxoglutarate, 3-Mercaptopropionic acid, Aminooxyacetic acid and Glutarate.

The GABA transporter inhibitor may consist of tiagabine. The GABA receptors agonists and modulators: may be selected from the group consisting of topiramate, felbamate, tramadol, Oxcarbazepine, Carbamazepine, eszopiclone, zopiclone, baclofen, gamma-Hydroxybutyric acid, imidazopyridines like zaleplon, zolpidem, zopiclone phenyloin, propofol, phenyloin, benzodiazepines and barbiturates.

Benzodiazepines may be selected from the group consisting of clobazam, Alprazolam (Xanax®), Bromazepam (Lexomil®), Diazepam (Valium®), Lorazepam (Ativan®), Clonazepam (Klonopin®), Temazepam (Restoril®), Oxazepam (Serax®), Flunitrazepam (Rohypnol®), Triazolam (Halcion®), Chlordiazepoxide (Librium®), Flurazepam (Dalmane®), Estazolam (ProSom®), and Nitrazepam (Mogadon®).

Barbiturates may be selected from the group consisting of primidone and phenobarbitone, pentobarbital, midazolam, phenyloin, secobarbital and amobarbital butabarbital barbital, phenobarbital, butalbital, cyclobarbital, allobarbital, methylphenobarbital, and vinylbital.

The present invention also pertains to pharmaceutical compositions comprising taurine, a taurine precursor, a taurine metabolite, a taurine derivative, a taurine analog and a substance required for the taurine biosynthesis and wherein the said pharmaceutical compositions are aimed at preventing or inhibiting the undesirable side-effects caused to a human or an animal organism by an active ingredient that induces a high level of extracellular GABA or increases GABA transmission.

This invention also relates to therapeutic methods for preventing or inhibiting the undesirable side-effects caused to a human or an animal organism by an active ingredient that induces a high level of extracellular GABA or increases GABA transmission, wherein the said therapeutic methods comprise a step of administering, to a human or an animal organism in need thereof, an effective amount of a substance selected from the group consisting of taurine, a taurine precursor, a taurine metabolite, a taurine derivative, a taurine analog and a substance required for the taurine biosynthesis.

These compositions and methods are described in more detail hereunder.

Pharmaceutical Compositions and Methods.

Generally, a pharmaceutical composition according to the invention comprises the combination of:
(i) a first active ingredient that induces a high level of extracellular GABA or increases GABA transmission; and
(ii) a second active ingredient selected from the group consisting of taurine, a taurine precursor, a taurine metabolite, a taurine derivative, a taurine analog and a substance required for the taurine biosynthesis, and further also one or more pharmaceutically acceptable excipients.

Thus, the said second active ingredient is selected from the group consisting of taurine and "taurine-like" substances.

In a pharmaceutical composition according to the invention, a preferred active ingredient that induces a high level of extracellular GABA, i.e. the first active ingredient, consists of 4-amino-5-hexenoic acid (vigabatrin), the racemic mixture or the active isomer.

The pharmaceutical compositions according to the invention are aimed at preventing various neurological disorders including primarily convulsive disorders. Convulsive disorders encompass epilepsy, tuberous sclerosis, infantile spasms as well as the convulsive disorders affecting patients undergoing a drug addiction, including a drug addiction to heroin or cocaine, ethanol.

Thus, a pharmaceutical composition according to the invention consists primarily of an anti-convulsive pharmaceutical composition.

The first and the second active ingredients are comprised in an anticonvulsive pharmaceutical composition in a "therapeutically effective amount", that is in an amount sufficient for the combination of active ingredients to exert the expected anticonvulsive effect while inducing no deleterious side effect, or side effects which are reduced as compared with the deleterious side effects induced by pharmaceutical compositions comprising the first active ingredient without taurine nor a taurine-like substance.

Generally speaking, a "therapeutically effective amount", or "effective amount", or "therapeutically effective", as used herein, refers to that amount which provides a therapeutic effect for a given condition and administration regimen. This is a predetermined quantity of active material calculated to produce a desired therapeutic effect in association with the required additive and diluent; i.e., a carrier, or administration vehicle. Further, it is intended to mean an amount sufficient to reduce and most preferably prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluents; i.e., carrier, or additive.

The present invention also deals with methods for preventing or inhibiting the undesirable side-effects caused to a human or an animal organism by an active ingredient that induces a high level of extracellular GABA or increases GABA transmission, wherein the said methods comprise a step of administering, to a human or an animal organism in need thereof, an effective amount of taurine or of a taurine-like substance.

The present invention also concerns methods for preventing or treating convulsive disorders comprising a step of administering, to a human or an animal organism in need thereof, a combination of:
(i) a first active ingredient that induces a high level of extracellular GABA or increases GABA transmission; and
(ii) a second active ingredient selected from the group consisting of taurine, a taurine precursor, a taurine metabolite, a taurine derivative, a taurine analog and a substance required for the taurine biosynthesis, Typically, the first active ingredient consists of 4-amino-5-hexenoic acid (vigabatrin).

In an advantageous embodiment, the second active ingredient is selected form the group consisting of taurine and vitamin B6.

The individuals in need of such treatments encompass those, either adult or child patients, which are susceptible to convulsive disorders, especially epilepsy.

In certain embodiments, the said method comprises a step of administering to a patient in need thereof a pharmaceutical composition that is described in the present specification.

In a pharmaceutical composition according to the invention, the amount of the first active ingredient, i.e. the active ingredient that induces a high level of extracellular GABA, is the amount of the said active ingredient that is conventionally used for treating patients affected with convulsive disorders. Typically, for vigabatrin, the said pharmaceutical composition is adapted so that the dosage form used allows the administration of an amount of vigabatrin ranging between 10 µg and 10 grams per day, preferably between 100 µg and 5 grams, including between 1 mg and 1 gram, for a human adult patient having a mean weight of 80 kilos. Typically, a dosage form will contain half the daily dose, for the purpose of performing two takes per day. Lower amounts of vigabatrin may be used, especially when the active ingredient is not under the racemic form but instead under the form of its active isomer, which lower amounts are typically half the amount of the racemic form which would have been conventionally used.

In a pharmaceutical composition according to the invention, the amount of the second active ingredient, i.e. taurine or a taurine-like substance, is adapted so that the said pharmaceutical composition is adapted so that the dosage form used allows the administration of an amount of taurine or of the taurine-like substance ranging from 10 µg to 10 grams per day for a human adult patient having a mean weight of 80 kilos.

Indeed, in a pharmaceutical composition or in a pharmaceutical method according to the invention, the active ingredient(s) is (are) used in combination with one or more pharmaceutically or physiologically acceptable excipients.

Generally, a pharmaceutical composition according to the invention, irrespective of whether the said composition (i) comprises only one or more substances selected from taurine and taurine-like substances or (ii) comprises a combination of a first active ingredient that induces a high level of extracellular GABA and a second active ingredient selected from taurine and taurine-like substances, comprises the one or more active ingredients in an amount ranging from 0.1% to 99.9% by weight, and usually from 1% to 90% by weight, based on the total weight of the said pharmaceutical composition.

Generally, a pharmaceutical composition according to the invention comprises an amount of excipient(s) that ranges from 0.1% to 99.9% by weight, and usually from 10% to 99% by weight, based on the total weight of the said pharmaceutical composition.

By "physiologically acceptable excipient or carrier" is meant solid or liquid filler, diluents or substance which may be safely used in systemic or topical administration.

Depending on the particular route of administration, a variety of pharmaceutically acceptable carriers well known in the art include solid or liquid fillers, diluents, hydrotropes, surface active agents, and encapsulating substances.

Pharmaceutically acceptable carriers for systemic administration that may be incorporated in the composition of the invention include sugar, starches, cellulose, vegetable oils, buffers, polyols and alginic acid. Specific pharmaceutically acceptable carriers are described in the following documents, all incorporated herein by reference: U.S. Pat. No. 4,401,663, Buckwalter et al. issued Aug. 30, 1983; European Patent Application No. 089710, LaHann et al. published Sep. 28, 1983; and European Patent Application No. 0068592, Buckwalter et al. published Jan. 5, 1983. Preferred carriers for parenteral administration include propylene glycol, pyrrolidone, ethyl oleate, aqueous ethanol, and combinations thereof.

Representative carriers include acacia, agar, alginates, hydroxyalkylcellulose, hydroxypropyl methylcellulose, carboxymethylcellulose, carboxymethylcellulose sodium, carrageenan, powdered cellulose, guar gum, cholesterol, gelatin, gum agar, gum arabic, gum karaya, gum ghatti, locust bean gum, octoxynol 9, oleyl alcohol, pectin, poly(acrylic acid) and its homologs, polyethylene glycol, polyvinyl alcohol, polyacrylamide, sodium lauryl sulfate, poly(ethylene oxide), polyvinylpyrrolidone, glycol monostearate, propylene glycol monostearate, xanthan gum, tragacanth, sorbitan esters, stearyl alcohol, starch and its modifications. Suitable ranges vary from about 0.5% to about 1%.

For formulating a pharmaceutical composition according to the invention, the one skilled in the art will advantageously refer to the last edition of the European pharmacopoeia or of the United States pharmacopoeia.

Preferably, the one skilled in the art will refer to the fifth edition "2005" of the European Pharmacopoeia, or also to the edition USP 28-NF23 of the United States Pharmacopoeia.

The weight amount of the combination of active ingredients that is contained in each dose of the pharmaceutical composition of the invention will depend on the molecular weight of said therapeutically active compound as well as on the weight amount that is effective in inhibiting or blocking the convulsive disorder. Effective amounts of extracellular GABA inducers, and specifically of vigabatrin, that are needed for preventing or treating convulsive disorders are well known from the one skilled in the art.

For determining the appropriate amount of taurine or of the taurine-like substance(s) to be combined with the extracellular GABA inducer, e.g. vigabatrin, in a dose of a pharmaceutical composition of the invention, the one skilled in the art may advantageously refer to the effective amounts that are already known or determined in the art for the taurine or taurine-like substance(s) that is (are) comprised therein.

The present invention is further illustrated by the examples below.

EXAMPLES

Examples 1 and 2

A. Materials and Methods of Examples 1 and 2

Vigabatrin Treatment

As described previously (Duboc et al., 2004), Wistar rats Rj Wi IOPS Han and Balb c mice were purchased from Janvier Breeding Center (Le Genest St Isle, France) at 7 weeks. VGB was dissolved in 0.9% NaCl at a concentration of 125 mg/ml. It was administered at 40 mg (125 mg/ml, 0.32 ml) by daily intraperitoneal injection for 45 or 65 days and at 3 mg (60 mg/ml, 0.05 ml) to mice for 29 days (daily dose of about 200 mg/kg in rats and 150 mg/kg in mice). Vitamin B6 (active form) was administered at a dose of 1 mM/kg (solution 154.46 mg/ml) whereas taurine was provided in the drinking water at 0.1 mol/l.

ERG were recorded as described previously after the last VGB injection (Duboc et al., 2004). Anesthesia was induced by an intramuscular injection of a solution containing ketamine (100 mg/kg) and xylazine (10 mg/kg). After 10 min adaptation to a 2.5 cdm$^{-2}$ light intensity, ten recordings were obtained with flash intensity of 10 cdsm$^{-2}$ at an interstimulus interval 30 s and subsequently averaged. These photopic ERG measurements were performed after 59 days in rats and 29 days in mice.

After 65 days of injection, rats were anesthetized for blood sampling. Anesthesia was induced as described above. Under anesthesia an indwelling catheter was placed in the carotid artery. This method allowed obtaining a single, large, good quality blood sample. A 1 mL blood sampling was taken for each rat in a heparinized blood sampler, immediately centrifuged and frozen at −80° C. Automated amino acid ion chromatography (Pasteur Cerba, France) was used for the quantitative determination of total and free amino acids in the samples.

Example 1

Taurine Deficiency Induced by the Extracelular GABA Inducer Vigabatrin

In Table 1, the amino acid concentrations measured on blood samples for both vigabatrin-treated and control albino animals are presented. It indicates that concentration differences ranging from 7 to 32% were not statistically significant for most amino acids threonine, serine, valine, citrulline, alanine, glycine, proline, glutamine, isoleucine, leucine, tyrosine, phenylalanine, arginine, histidine, lysine, ornithyne. As previously reported the glutamic acid was greatly reduced by 56% in the blood sample and this difference was statistically significant. However, the greatest change was observed for taurine which was decreased by 67% in vigabatrin-treated animals from 373.4 to 122.2 µM. This difference was statistically significant ($p<0.05$). A significant difference (22%) was also observed for methionine. These observations indicated that taurine and methionine concentrations are significantly reduced by the vigabatrin treatment.

Example 2

Figure 1:
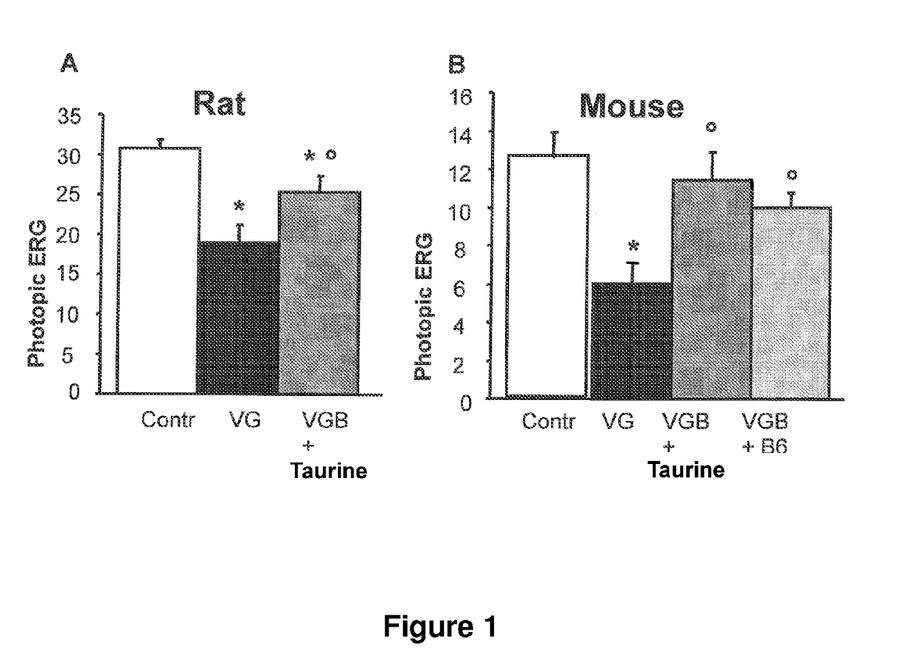
FIG. 1 illustrates the neuroprotection by taurine or vitamin B6 against the side effects caused by the extracellular GABA-inducer vigabatrin.

Prevention and Treatment of the Undesirable Side Effects Caused by the Extracellular GABA Inducer Vigabatrin by Taurine and a Taurine-Like Substance To investigate whether taurine supplementation could prevent the vigabatrin-induced retinal toxicity, animals were treated with vigabatrin alone or vigabatrin plus a taurine supplementation. Vigabatrin alone induced a decrease in the photopic electroretinogram (ERG) measurement as previously described. By contrast, in mice, the difference was no longer statistically significant between controls and vigabatrin plus taurine supplementation or vigabatrin plus vitamin B6 supplementation (FIG. 1B). In rats, although the photopic ERG amplitude decreased less than in vigabatrin alone, the difference remained statistically significant with the group of control animals (FIG. 1A). However, in all species, the difference between vigabatrin and vigabatrin plus taurine supplementation was statistically significant in treated animals (FIG. 1). Similarly, the supplementation with vitamin B6 also reduced the decrease in photopic ERG amplitude and the difference between the mouse group of vigabatrin alone and the group receiving vigabatrin plus vitamin B6 supplementation was statistically significant (FIG. 1B). These results are consistent with the hypothesis that vigabatrin-induced decrease in taurine concentration could produce the retinal toxicity of vigabatrin.

TABLE 1

Blood concentrations for amino acids in albino rats treated with vigabatrin (VGB) or not treated (control).

|  | Control | VGB |
| --- | --- | --- |
| Taurine | 373.4 ± 46.7 | 122.2 ± 26.6 * |
| Thréonine | 194.2 ± 30.8 | 130.6 ± 7.0 |
| Sérine | 203.8 ± 28.7 | 169.4 ± 16.1 |
| Acide glutamique | 217.4 ± 56.6 | 94.8 ± 15.6 * |
| Valine | 167.4 ± 14.8 | 146 ± 8.9 |
| Citrulline | 54 ± 9.7 | 45.6 ± 4.2 |

TABLE 1-continued

Blood concentrations for amino acids in albino rats treated
with vigabatrin (VGB) or not treated (control).

|  | Control | VGB |
|---|---|---|
| Alanine | 303.8 ± 32.3 | 270.4 ± 29.5 |
| Glycine | 190.6 ± 30.1 | 142.8 ± 17.6 |
| Proline | 155 ± 21.0 | 110.6 ± 20.1 |
| Glutamine | 375.6 ± 40.7 | 349 ± 13.4 |
| Methionine | 58 ± 4.7 | 45 ± 1.4 * |
| Isoleucine | 79.8 ± 8.0 | 68.2 ± 4.5 |
| Leucine | 152.6 ± 17.6 | 123.2 ± 11.5 |
| Tyrosine | 63.2 ± 6.8 | 51.6 ± 4.5 |
| Phenylalanine | 54.2 ± 6.9 | 42.8 ± 1.0 |
| Arginine | 130 ± 39.0 | 111.8 ± 15.1 |
| Histidine | 75.8 ± 5.4 | 63.2 ± 2.9 |
| Lysine | 307.2 ± 23.8 | 260.4 ± 32.3 |
| Ornithine | 78.6 ± 33.0 | 57.6 ± 10.6 |

Measures are provided in μM (n = 5, s.e.m.).

Examples 3 and 4

A. Materials and Methods of Examples 3 and 4

A.1. Animal Treatments

As described previously (Duboc, A., et al. Vigabatrin, the GABA-transaminase inhibitor, damages cone photoreceptors in rats. *Annals of neurology* Vol. 55, 695-705 (2004).), Wistar rats Rj Wi IOPS Han or BALB/c mice were purchased from Janvier (Le Genest-St-Isle, France) at between six and seven weeks of age. VGB dissolved in 0.9% NaCl was administered at 40 mg (125 mg/ml, 0.32 ml) to rats by daily intraperitoneal injection for 45 or 65 days and at 3 mg (60 mg/ml, 0.05 ml) to mice for 29 days. These daily doses (rats: 200 mg/kg; mice: 150 mg/kg) are in-line with those described for the treatment of epilepsy in animals (Andre, V., Ferrandon, A., Marescaux, C. & Nehlig, A. Vigabatrin protects against hippocampal damage but is not antiepileptogenic in the lithium-pilocarpine model of temporal lobe epilepsy. *Epilepsy research* Vol. 47, 99-117 (2001)) or in humans (adult patients: 1-6 mg/kg; children: 50-75 mg/kg; or infants: 100-400 mg/kg) (Chiron, C., Dumas, C., Jambaque, I., Mumford, J. & Dulac, O. Randomized trial comparing vigabatrin and hydrocortisone in infantile spasms due to tuberous sclerosis. *Epilepsy research* Vol. 26, 389-395 (1997); Lux, A. L., et al. The United Kingdom Infantile Spasms Study comparing vigabatrin with prednisolone or tetracosactide at 14 days: a multicentre, randomised controlled trial. *Lancet* Vol. 364, 1773-1778 (2004); Aicardi, J., Mumford, J. P., Dumas, C. & Wood, S. Vigabatrin as initial therapy for infantile spasms: a European retrospective survey. Sabril IS Investigator and Peer Review Groups. *Epilepsia* Vol. 37, 638-642 (1996)). Taurine supplementation was given in drinking water at a concentration of 0.1M. Light intensity in the animal cages ranged between 125 and 130 lux for rats and between 70 and 85 lux for mice.

A.2. Electroretinogram (ERG)

Figure 2:
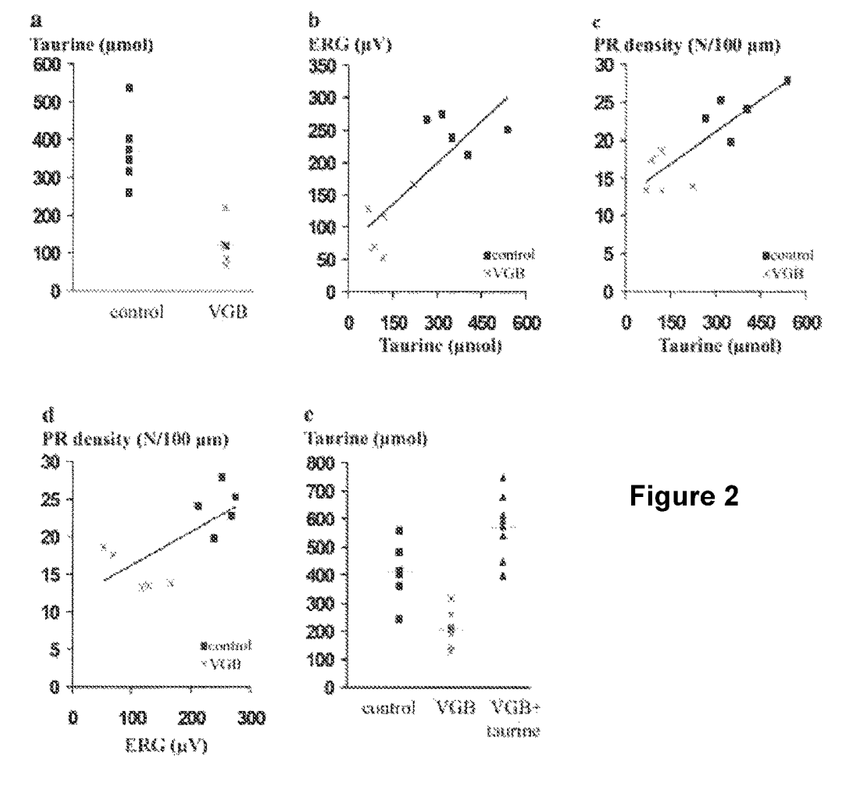
FIG. 2 illustrates the correlation between taurine plasma levels and the retinal toxicity of vigabatrin.

Photopic ERGs were recorded after the last VGB injection, as described previously (Duboc, A., et al. Vigabatrin, the GABA-transaminase inhibitor, damages cone photoreceptors in rats. *Annals of neurology* Vol. 55, 695-705 (2004).). Anesthesia was induced by intraperitoneal injection (0.8 to 1.2 ml/kg) of a solution containing ketamine (40 mg/ml) and xylazine (4 mg/ml Rompum). Animals were light-adapted for 10 minutes with a background light of 25 cdm$^{-2}$. Light flashes were then applied on this background light; the light intensity of the flash was 10 cdsm$^{-2}$ for the mouse experiments and for the rats maintained in darkness (FIGS. 2, 6) or 25 cdsm$^{-2}$ for other experiments (FIGS. 3, 5). Ten recordings were averaged with an interstimulus interval of 30 s.

A.3. Histology

Eye cups were fixed overnight at 4° C. in 4% (wt/vol) paraformaldehyde in phosphate buffered saline (PBS; 0.01M, pH 7.4). The tissue was cryoprotected in successive solutions of PBS containing 10%, 20% and 30% sucrose at 4° C., oriented along the dorso-ventral axis and embedded in OCT (Labonord, Villeneuve d'Ascq, France). Retinal sections (8-10 μm thickness) were permeabilised for five minutes in PBS containing 0.1% Triton X-100 (Sigma, St. Louis, Mo.), rinsed, and incubated in PBS containing 1% bovine serum albumin (Eurobio, Les-Ulis, France), 0.1% Tween 20 (Sigma), and 0.1% sodium azide (Merck, Fontenay-Sous-Bois, France) for two hours at room temperature. The primary antibody added to the solution was incubated for two hours at room temperature. Polyclonal antibodies were directed against VGluT1 (1:2000, Chemicon), rabbit GFAP (1/400, Dako, USA) and mouse cone arrestin (Zhu, X., et al. Mouse cone arrestin expression pattern: light induced translocation in cone photoreceptors. *Molecular vision* Vol. 8, 462-471 (2002)) (Luminaire junior, LUMIj, 1:20,000). Monoclonal antibodies were directed against Goa (1:2000, Chemicon). Sections were rinsed and then incubated with the secondary antibody, goat anti-rabbit IgG or rabbit anti-mouse IgG conjugated to either Alexa TM594 or Alexa TM488 (1:500, Molecular Probes, Eugene, Oreg.) for two hours. Inner/outer segments of cone photoreceptors were stained with a peanut lectin (PNA, Sigma) during 12 hours of incubation at 4° C. The dye, diamidiphenyl-indole (DAPI), was added during the final incubation period. Sections were rinsed, mounted with Fluorsave reagent (Calbiochem, San Diego, Calif.) and viewed with a Leica microscope (LEICA DM 5000B) equipped with a Ropper scientific camera (Photometrics cool SNAP TM FX).

For quantification, vertical sections along the dorso-ventral axis were selected at the optic nerve. Following DAPI nuclear staining, the lengths of disorganised retinal areas were measured; GFAP immunostaining was used for detection and quantificationof retinal areas with reactive gliosis. The cone photoreceptor density was calculated following cone arrestin immunostaining (rats) or PNA labelling (mice) to visualise the inner/outer segments of cone photoreceptors; areas with disorganised retinal layering were excluded. Areas with sprouting bipolar cells were quantified following immunolabeling of these cells with the antibody directed against the protein Goa.

A.4. Amino-Acid Measurements

Blood samples were collected in haemolysis tubes containing heparin (14 IU/ml) and centrifuged (2200 g, 15 min). Plasma amino-acid analysis was performed by ion-exchange chromatography with nihydrin detection using a JEOL AMINOTAC analyser.

B. Results

Example 3

The Retinal Toxicity of Vigabatrin Relies on Taurine Deficiency

Taurine deficiency is known to induce photoreceptor degeneration in mice (Rascher et al., 2004), rats (Lake and Malik, 1987), cats (Leon et al., 1995) and monkeys (Imaki et al., 1987). Although taurine levels had instead been reported to be unchanged or increased in vigabatrin-treated animals (Halonen et al., 1990; Neal and Shah, 1990) and patients (Halonen et al., 1988; Pitkanen et al., 1988), we examined the potential role of taurine in VGB retinal toxicity. Plasma amino-acid levels were measured in control animals and VGB-injected rats treated for 65 days. The differences in concentrations for most amino acids (threonine, serine, valine, citrulline, alanine, glycine, proline, glutamine, isoleucine, leucine, tyrosine, phenylalanine, arginine, histidine, lysine, and ornithine) were not statistically different between the two groups of animals. By contrast, the plasma glutamic acid concentrations were much lower (by 56%) in VGB-treated animals than in control animals, consistent with previous reports anticonvulsant effects in mice. *J Neural Transm* Vol. 72, 213-233 (1988)); this difference was statistically significant (control: 217.4±56.6 µM; VGB: 94.8±15.6 µM s.e.m., n=5), as already shown in Table 1 of example 2. However, the greatest difference was observed for taurine. Taurine levels were by 67% lower in VGB-treated animals (122.2±26.6 µM) than in control animals (373.4±46.7 µM) (FIG. 2A, p<0.05, n=5, s.e.m.). A significant difference (22% reduction) was also observed for methionine. To determine if this decrease in taurine level is correlated to visual loss, both ERG amplitudes (r=0.769, p=0.0093%) and cone densities (r=0.818, p=0.0038%) were plotted against taurine levels in control animals and VGB-treated rats (FIGS. 2B, 2C). Taurine levels were highly correlated to both ERG amplitudes and cone densities; these two factors were also correlated with each other (FIG. 2D, r=0.703, p=0.0023%). Thus, the low level of circulating taurine may directly contribute to retinal VGB toxicity in rats.

Figure 3A:
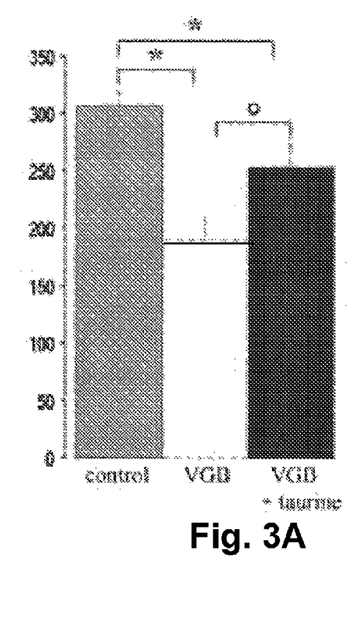
FIG. 3 illustrates the prevention by taurine supplementation of all features of vigabatrin-induced retinal toxicity in rats.
Figure 3B:
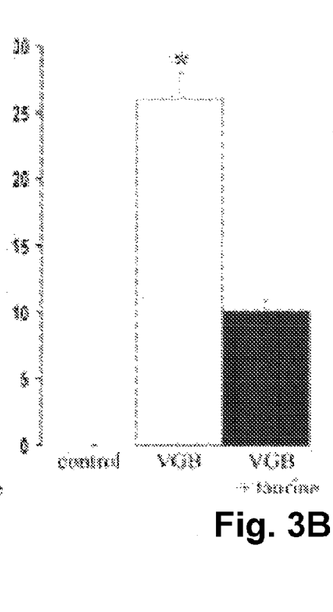
Figure 3C:
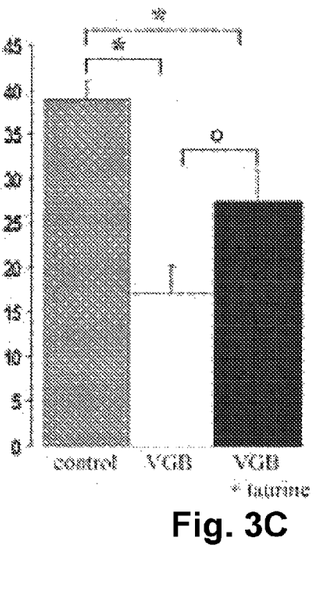
Figure 3D:
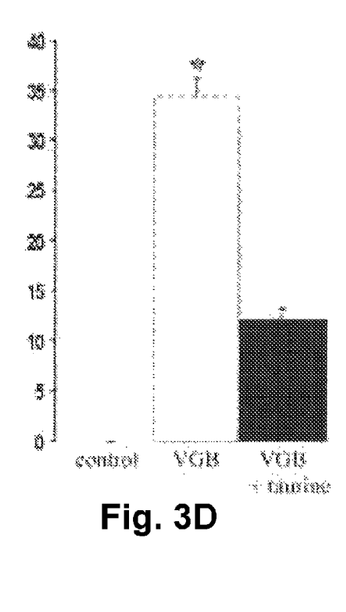

Taurine is mainly obtained from nutrition; thus, we supplemented the drinking water of one group of VGB-treated rats with taurine (0.1M) (n=7). The plasma levels of taurine in these animals increased above those of control animals and above those of VGB-treated animals without taurine supplementation (FIG. 2E). The photopic ERG amplitude was greater in VGB-treated animals receiving taurine supplementation than in VGB-treated animals without taurine supplementation (n=7) (FIG. 3A, ° p<0.01), but remained lower than in control animals (n=5) (FIG. 3A, * p<0.05). Similarly, the cone segment density was greater in the VGB-treated group with taurine supplementation than in animals without supplementation (FIG. 3B, ° p<0.05), but remained lower than that of the control group (FIG. 3B, * p<0.001). Furthermore, the VGB-induced increase in GFAP immunostaining was less extensive in animals receiving taurine supplementation than in animals without supplementation (FIG. 3C, ° p<0.001). These findings show that VGB-induced retinal damage can be attenuated by taurine supplementation in rats.

Figure 4:
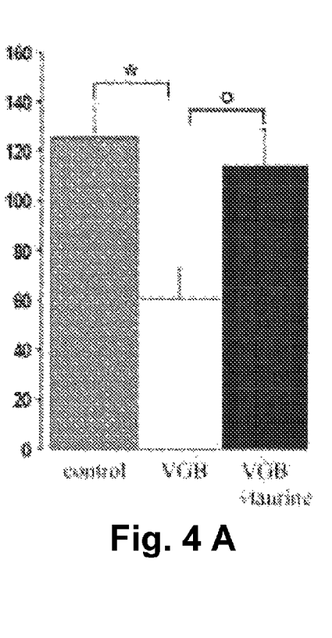
FIG. 4 illustrates the prevention by taurine supplementation of all features of vigabatrin-retinal toxicity in mice.
Figure 4B:
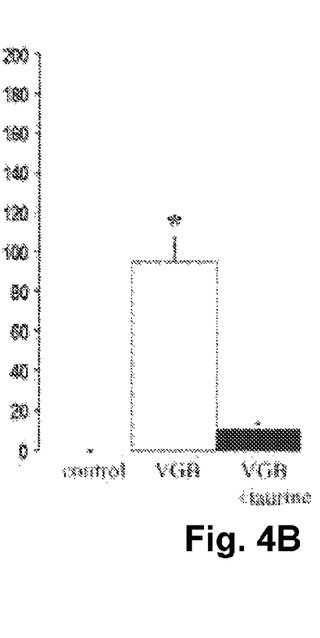
Figure 4C:
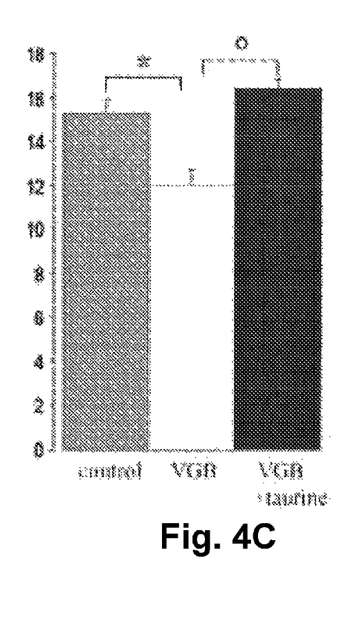
Figure 4D:
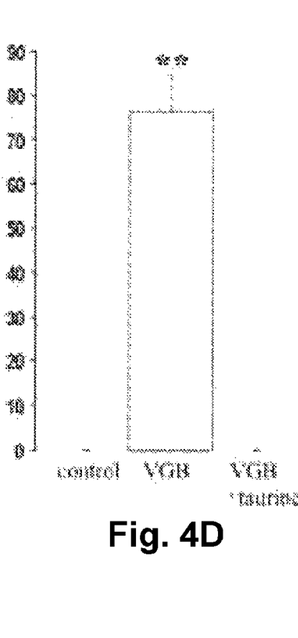

To determine whether taurine can prevent VGB retinal toxicity in another species, mice were administered VGB with (n=7) or without taurine supplementation (n=7) for 29-30 days. As in rats, VGB-treated mice had significantly lower photopic ERG amplitude than the control group (n=5) (FIG. 4A, * p<0.01). Taurine supplementation suppressed this decrease in photopic ERG amplitude such that the difference between these mice and the control group was not statistically different. The difference between the two VGB-treated groups with or without taurine supplementation was statistically significant (FIG. 4A, ° p<0.05). Quantification of the disorganisation of the outer nuclear layer in the two VGB-treated groups showed that mice with taurine supplementation had smaller areas of retinal disorganisation than mice without supplementation (FIG. 4B, ° p<0.001). Quantification of cone outer and inner segments following lectin staining of their extracellular matrix indicated that VGB treatment resulted in lower densities (FIG. 4C, * p<0.001). Taurine supplementation prevented this decrease in cone density (FIG. 4D, ° p<0.001). Finally, the sprouting of bipolar cell dendrites, observed in VGB-treated mice, was completely suppressed by the taurine supplementation. These results indicate that taurine supplementation also reduces features of VGB toxicity in mice.

Example 5

Taurine Deficiency in Infants Receiving Vigabatrin Therapy

We then evaluated whether these findings have any clinical relevance in patients with epilepsy. Plasma taurine levels were reviewed retrospectively in patients presenting infantile spasms, who had received VGB treatment for at least six months in Necker Hospitals for the last 3 years. Plasma amino-acid levels are routinely measured in patients with infantile spasms as part of their etiological work-up, particularly when brain RMI is negative. Data were available in six patients (Table 2 hereunder). Five patients had a taurine level below normal values for infants of a similar age; taurine was undetectable in two patients. For one of these two patients (patient 2), the taurine level was measured before starting a 15 month period of VGB therapy and this taurine level was normal. In patient 6, the taurine level was in the lower part of the normal range, but this measurement could have been overestimated by the delayed blood centrifugation. Thus, taurine levels seem to be decreased in VGB-treated epileptic infants.

TABLE 2

| Patients | 1 | 2 | 3 | 4 | 5 | 6 |
|---|---|---|---|---|---|---|
| Age at VGB onset | 6 m | 9 m | 7 m | 3 m | 3 m | 6 m |
| Age at taurine measurement | 2.5 y | 8.5 m    2 y | 3 y | 1.2 y | 9 m | 2.1 y |
| Taurine level (µmoles/l) | und* | 75    und | 26 | 20 | 38 | 52 |
| Normal values (µmoles/l ± SD) at corresponding age | 70 ± 22 | 81 ± 35    70 ± 22 | 70 ± 22 | 76 ± 36 | 81 ± 35 | 70 ± 22 |
| Delay between blood sampling and plasma preparation | <2 h | <2 h    <2 h | <2 h | <2 h | 48 h | 72 h | und*: undetectable
SD: Standard Deviation

REFERENCE

Duboc A, Hanoteau N, Simonutti M, Rudolf G, Nehlig A, Sahel J A, Picaud S (2004) Vigabatrin, the GABA-transaminase inhibitor, damages cone photoreceptors in rats. Ann Neurol 55:695-705.

Halonen T, Pitkanen A, Riekkinen P J (1990) Administration of vigabatrin (gamma-vinyl-gamma-aminobutyric acid) affects the levels of both inhibitory and excitatory amino acids in rat cerebrospinal fluid. J Neurochem 55:1870-1874.

Halonen T, Lehtinen M, Pitkanen A, Ylinen A, Riekkinen P J (1988) Inhibitory and excitatory amino acids in CSF of patients suffering from complex partial seizures during chronic treatment with gamma-vinyl GABA (vigabatrin). Epilepsy Res 2:246-252.

Imaki H, Moretz R, Wisniewski H, Neuringer M, Sturman J (1987) Retinal degeneration in 3-month-old rhesus monkey infants fed a taurine-free human infant formula. J Neurosci Res 18:602-614.

Lake N, Malik N (1987) Retinal morphology in rats treated with a taurine transport antagonist. Exp Eye Res 44:331-346.

Leon A, Levick W R, Sarossy M G (1995) Lesion topography and new histological features in feline taurine deficiency retinopathy. Exp Eye Res 61:731-741.

Neal M J, Shah M A (1990) Development of tolerance to the effects of vigabatrin (gamma-vinyl-GABA) on GABA release from rat cerebral cortex, spinal cord and retina. Br J Pharmacol 100:324-328.

Pitkanen A, Matilainen R, Ruutiainen T, Lehtinen M, Riekkinen P (1988) Effect of vigabatrin (gamma-vinyl GABA) on amino acid levels in CSF of epileptic patients. J Neurol Neurosurg Psychiatry 51:1395-1400.

Rascher K, Servos G, Berthold G, Hartwig H G, Warskulat U, Heller-Stilb B, Haussinger D (2004) Light deprivation slows but does not prevent the loss of photoreceptors in taurine transporter knockout mice. Vision Res 44:2091-2100.

The invention claimed is:

1. A method of limiting or reducing the incidence of visual side-effects caused by an active ingredient that increases GABA levels or activates GABA receptors in a mammal, the method comprising administering to a subject in need thereof an effective amount of taurine; wherein said active ingredient that increases GABA levels or activates GABA receptors is at least one selected from the group consisting of:

a GABA-aminotransferase inhibitor selected from the group consisting of: 4-amino-5-hexenoic acid, its racemic mixture or an active isomer, valproate, (1R,3S,4S)-3-amino-4-fluorocyclopentane-1-carboxylic acid, (1R,4S)-4-amino-2-cyclopentene-1-carboxylic acid, (1S,4R)-4-amino-2-cyclopentene-1-carboxylic acid, (4R)-4-amino-1-cyclopentene-1-carboxylic acid, (4S)-4-amino-1-cyclopentene-1-carboxylic acid, (S)-4-amino-4,5-dihydro-2-thiophenecarboxylic acid, 1H-tetrazole-5-(alpha-vinyl-propanamine), 2,4-diaminobutanoate, 2-oxoadipic acid, 2-oxoglutarate, 2-thiouracil, 3-chloro-4-aminobutanoate, 3-methyl-2-benzothiazolone hydrazone hydrochloride, 3-phenyl-4-aminobutanoate, 4-ethynyl-4-aminobutanoate, 5-diazouracil, 5-fluorouracil, aminooxyacetate, beta-alanine, cycloserine, and D-cycloserine, the GABA transporter blocker tiagabine, and a GABA receptor agonist or modulator selected from the group consisting of: topiramate, felbamate, tramadol, oxcarbazepine, carbamazepine, eszopiclone, zopiclone, baclofen, imidazopyridines, zaleplon, zolpidem, zopiclone phenytoin, propofol, phenytoin, benzodiazepines, and barbiturates; wherein the visual side-effect is at least one of damage to the retina, constriction of the visual field, dysfunction of central vision, reduced visual acuity, loss of color discrimination, and loss of contrast sensitivity.

2. The method according to claim 1, wherein the active ingredient that increases GABA levels or activates GABA receptors is tiagabine.

3. The method according to claim 1, wherein the active ingredient is administered to the subject as an anti-convulsive drug.

* * * * *